United States Patent [19]
Hake

[11] Patent Number: 5,141,500
[45] Date of Patent: * Aug. 25, 1992

[54] HYPODERMIC NEEDLE GUARD

[75] Inventor: Lawrence W. Hake, R.R. #2, Box 108, Grand Island, Nebr. 68803

[73] Assignee: Lawrence W. Hake, Grand Island, Nebr.

[*] Notice: The portion of the term of this patent subsequent to May 28, 2008 has been disclaimed.

[21] Appl. No.: 674,078

[22] Filed: Mar. 21, 1991

Related U.S. Application Data

[62] Division of Ser. No. 317,733, Mar. 2, 1989, Pat. No. 5,019,051.

[51] Int. Cl.$^5$ .............................................. A61M 5/32
[52] U.S. Cl. ................................ 604/198; 604/197; 604/263; 604/110
[58] Field of Search ............... 604/192, 197, 198, 263, 604/110

[56] References Cited

U.S. PATENT DOCUMENTS

| | | | |
|---|---|---|---|
| 4,425,120 | 1/1984 | Sampson et al. | 604/198 |
| 4,654,034 | 3/1987 | Masters et al. | 604/192 |
| 4,664,653 | 5/1987 | Sagstetter et al. | 604/197 |
| 4,664,654 | 4/1987 | Strauss | 604/198 |
| 4,666,435 | 5/1987 | Braginetz | 604/198 |
| 4,668,223 | 5/1987 | Grotenhuis | 604/191 |
| 4,681,567 | 4/1987 | Masters et al. | 604/198 |
| 4,693,708 | 9/1987 | Wanderer et al. | 604/198 |
| 4,695,274 | 9/1987 | Fox | 604/198 |
| 4,702,738 | 10/1987 | Spencer | 604/198 |
| 4,710,170 | 12/1987 | Haber et al. | 604/110 |
| 4,723,943 | 2/1988 | Spencer | 604/198 |
| 4,737,144 | 4/1988 | Choksi | 604/198 |
| 4,738,663 | 4/1988 | Bogan | 604/198 |
| 4,743,233 | 5/1988 | Schneider | 604/192 |
| 4,762,516 | 8/1988 | Luther | 604/164 |
| 4,772,272 | 9/1988 | McFarland | 604/198 |
| 4,778,453 | 10/1988 | Lopez | 604/110 |
| 4,816,022 | 3/1989 | Poncy | 604/198 |
| 4,846,796 | 4/1989 | Carrell | 604/110 |
| 4,927,417 | 5/1990 | Moncada et al. | 604/198 |
| 4,976,702 | 12/1990 | Andrews et al. | 604/198 |

Primary Examiner—Stephen C. Pellegrino
Assistant Examiner—Michael Rafa
Attorney, Agent, or Firm—Allegretti & Witcoff

[57] ABSTRACT

A needle guard for a syringe or other injection instrument with a sharp point is disclosed having a protective sleeve with a needle base, and having a retracted position and an irreversible extended position that may be used with a conventional syringe assembly. The needle guard being comprised of a needle base containing a hypodermic needle integral therewith and locking means, and a protective sleeve slidable on the needle base. Prior to and during use of the needle, the sleeve remains in a retracted position covering the barrel of the syringe. After the needle has been used, the sleeve is pushed forward into its locked extended position, so that the end of the sleeve extends beyond the tip of the needle. The tip of the needle is thereby shielded, preventing accidental sticks.

9 Claims, 4 Drawing Sheets

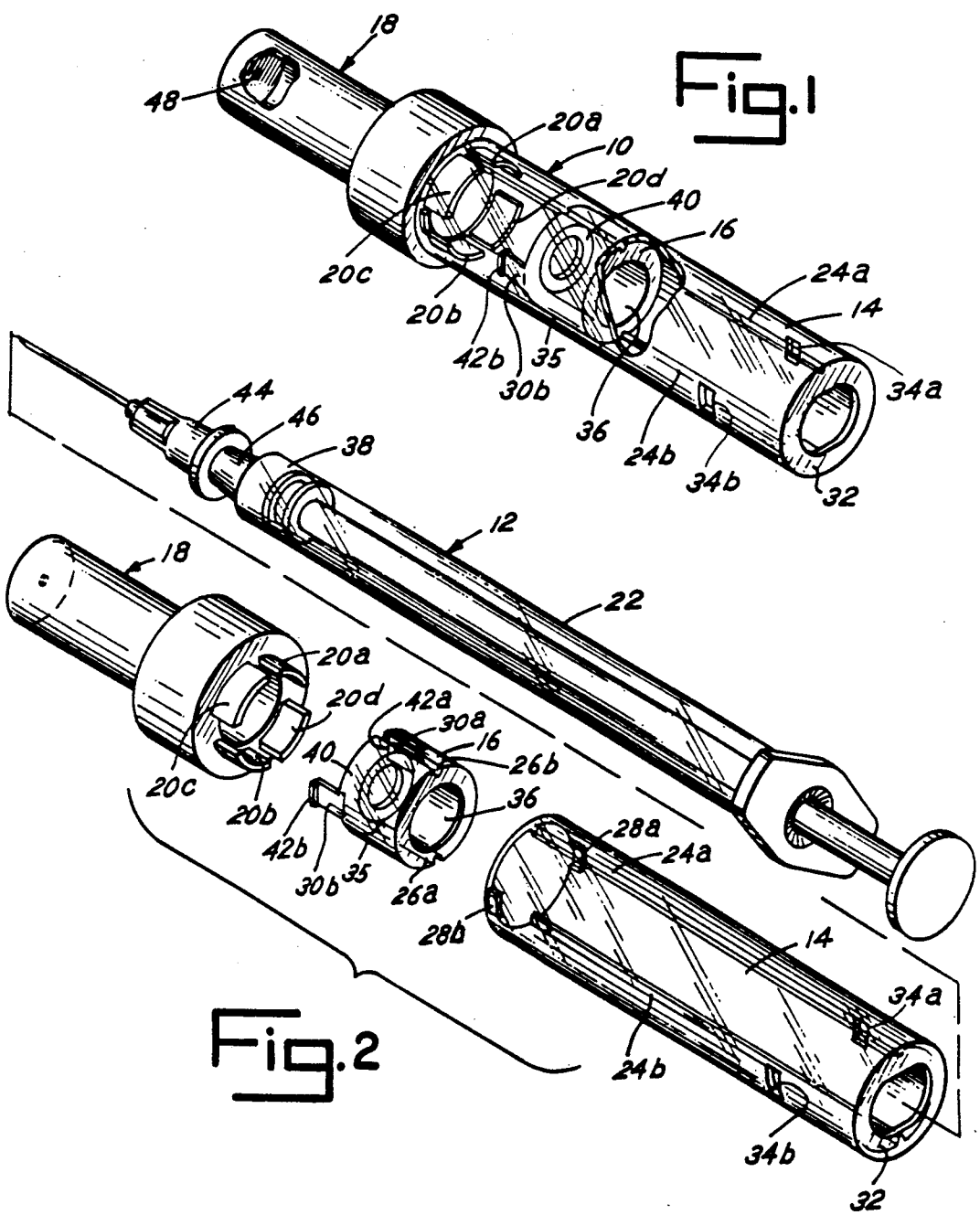

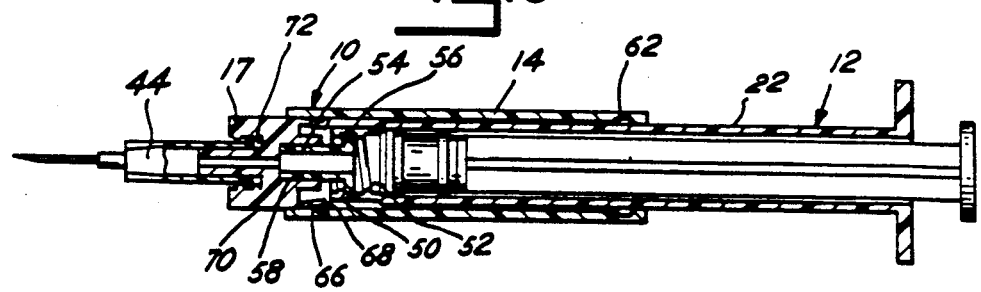
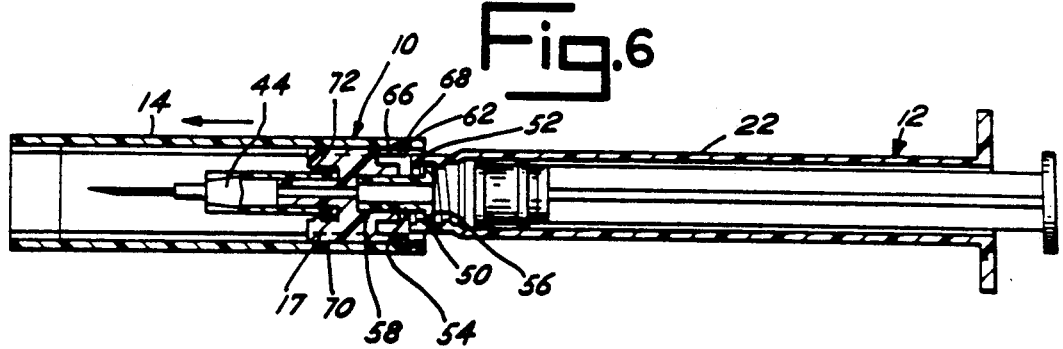
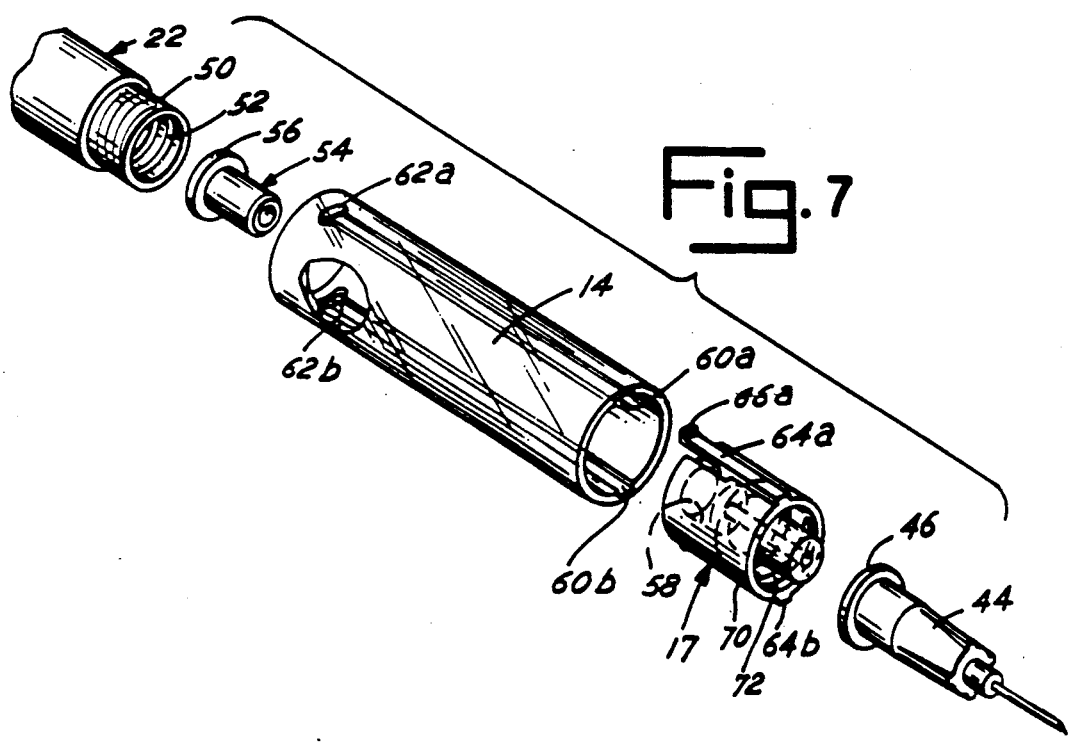

HYPODERMIC NEEDLE GUARD

BACKGROUND OF THE INVENTION

This is a division of my earlier filed, copending patent application, Ser. No. 317,733 filed Mar. 2, 1989, now U.S. Pat. No. 5,019,051.

This invention relates to syringes, and more particularly to a syringe construction designed for the prevention of needle-stick injuries.

Hypodermic syringes are widely used to inject substances into and to draw samples from human beings and animals. A hypodermic syringe typically includes a barrel that contains the substance to be injected or that is available to receive the sample to be drawn, and a needle which is connected to the barrel. Hypodermic syringes may be either reusable or disposable. Those that are disposable are normally discarded after use to avoid spread of contamination or disease.

It has been observed that there is a low but ever-present rate of needle-stick injuries suffered by medical practitioners after a syringe has been used. In one study of needle-stick injuries published recently, disposable syringes were involved in 6.9 needle-stick injuries per 100,000 items purchased, and accounted for 35 percent of the total number of needle-stick injuries from all sources. See Rates of Needle-Stick Injury Caused By Various Devices In A University Hospital, J. Jagger, M.P.H., Ph.D., E. H. Hunt, R.N., J. Brand-Elnaggar, B.A., & R. D. Pearson, M.D., 319 *New England Journal of Medicine*, 284–288, Aug. 4, 1988. The most common mechanism of injury from disposable syringes was due to attempts by hospital personnel to place a cap over the needle after use of the syringe, usually to protect themselves or others from the contaminated needle. The study concluded that efforts to implement safety guidelines have been ineffective and are unlikely to eliminate such injuries in the future. The study recommended redesign of instruments to eliminate use of needles, provide some sort of fixed barrier between the user and the needle, or allow the user's hands to remain behind the needle as it is covered.

Concern for the safety of health care workers has become acute in recent years, particularly due to the spread of the acquired immunodeficiency syndrome (AIDS). Indeed, needle-sticks by contaminated syringes have been attributed as the cause of infection in health care workers. Although an initial needle-stick injury may appear minor, the possibility of infection is serious enough to warrant efforts to eliminate the possibility of a needle-stick injury entirely.

A wide variety of hypodermic syringes have been proposed in an attempt to prevent needle-stick injuries. These structures generally require modification of the syringe barrel. For example, U.S. Pat. No. 4,737,144 to Choksi discloses a syringe with a sleeve which can be locked in a retracted position and also an extended position. The locking mechanism includes a slot formed near the end of the barrel which cooperates with spring urged tabs on the sleeve.

U.S. Pat. No. 4,425,120 to Sampson, et al., discloses a needle guard mounted on the barrel of the syringe. The guard can be releasably locked in the retracted position or locked in the extended position. Locking of the guard is effected by a track on the internal surface of the guard and track-engaging members on the barrel.

U.S. Pat. No. 4,573,976, also to Sampson, et al., discloses a similar structure with different locking means.

U.S. Pat. No. 4,356,822 to Winstead-Hall discloses a syringe assembly having a barrel and tubular guard with multiple locking members provided for securing the barrel and cap in a number of relative axial positions. A frangible end closure may be provided on the end of the cap closest to the needle. The locking members permit different locked positions for exposing different amounts of the needle.

Another approach is to provide a shield integral with the needle instead of the barrel. U.S. Pat. No. 3,134,380 to Armano discloses a collapsible needle guard integral with the needle portion of the syringe. The needle with guard is assembled and sterilized by the manufacturer. The purpose of the guard is to shield the needle from the view of the patient. None of these structures are known to be in widespread use. Most standard hypodermic syringe assemblies presently in use are unshielded and do not resolve the problem of needle sticks.

SUMMARY OF THE INVENTION

Briefly, the present invention comprises an improved needle guard that is compatible with the typical, unguarded hypodermic syringes currently in use. The needle guard is simple to use, inexpensive, does not require modification of the syringe in any way, and is effective to prevent needle-stick injuries. The needle guard places a fixed barrier between the hands of the syringe user and the point of the needle after use. It allows or requires the hands of the user to remain behind the needle as it is covered.

The needle guard includes a fitting or bushing cooperative with the barrel of the syringe and formed integrally with a hypodermic needle, together defining a needle base, and a slidable, protective sleeve which is retained on the needle base. A packaging cap is also provided as an optional feature. The needle base is fitted on the syringe barrel and is thus used to support the needle guard mounted on the syringe. To assemble the guard with the syringe, a user merely grasps the needle guard and orients the needle guard so that the open end of the protective sleeve faces the user. The user then slides the syringe barrel into the open end of the protective sleeve. The needle fitting end of the syringe barrel will protrude from the sleeve. The user then removes the packaging cap, and mounts the needle base on the needle fitting end of the barrel. The hypodermic syringe is now fully assembled with the needle guard sleeve in the retracted position so that needle is exposed and ready for use.

After use, the user grasps the sleeve and pushes it forward along the barrel in the direction of the needle. The user slides the sleeve forward until the needle base and sleeve irreversibly lock. The sleeve of the needle guard now extends beyond the pointed tip of hypodermic needle preventing access to the needle and thus preventing needle stick by the used needle.

The present invention is a substantial improvement relative to the prior art because it is convenient and practical. Accordingly, it is an object of this invention to provide an improved syringe construction which prevents needle-stick injuries and that is easy to use. Another object of the invention is to provide an improved syringe construction which is both safe and effective.

Yet another object of the invention is to provide a needle guard that is inexpensive, easily manufactured, and is useful with existing syringe constructions.

An additional object of the invention is to provide a needle guard utilizing an integral needle-bushing construction to further simplify the use of the invention. Other objects and advantages of the invention will become apparent from the following description of the invention.

BRIEF DESCRIPTION OF THE DRAWINGS

In the detailed description which follows, reference will be made to the drawings comprised of the following figures:

FIG. 1 is a perspective view of a first embodiment of the present invention, showing the needle guard with a packaging cap;

FIG. 2 is an exploded isometric view of the embodiment of FIG. 1 of the present invention showing the packaging cap, fitting or bushing, sleeve, and a standard hypodermic syringe;

FIG. 5 is a sectional view of a third embodiment of the present invention, showing the hypodermic syringe with a needle guard mounted between the hypodermic syringe and the hypodermic needle, in the retracted position;

FIG. 6 is a sectional view of the third embodiment of the present invention with the sleeve in the locked extended position;

FIG. 7 is an exploded isometric view of the third embodiment of the present invention showing the hypodermic syringe barrel, sleeve, bushing, and hypodermic needle;

DESCRIPTION OF PREFERRED EMBODIMENT

Figure 3:
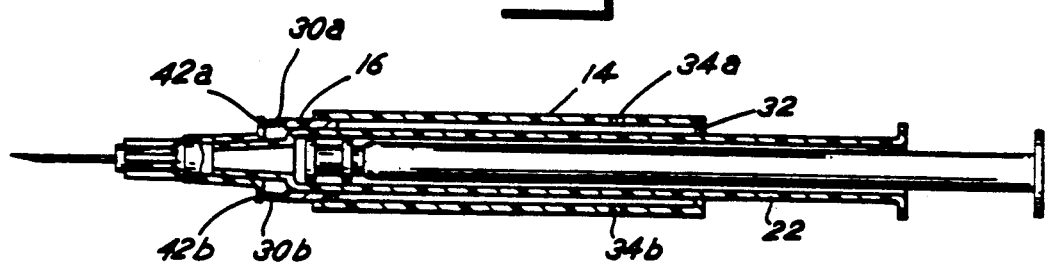
FIG. 3 is a sectional view of a syringe of a second embodiment of the needle guard in retracted position.

The present invention provides a unique and straightforward construction to prevent needle-stick injuries resulting from use of currently available syringes. The invention comprises an appliance for combination with syringes commonly in use. Thus as disclosed in FIGS. 1 and 2, the first embodiment of the improved needle guard 10 of the invention is compatible with a standard hypodermic syringe 12. The needle guard 10 is comprised of a protective sleeve 14 and a fitting or bushing 16, as well as an optional packaging cap 18. The needle guard 10 is mounted on the syringe 12, used therewith, and then the assembly is discarded. When the needle guard 10 is positioned upon the syringe 12, the bushing 16 frictionally fits on the barrel 22 of the syringe and slidably retains the sleeve 14. Sleeve 14 is slidable between a retracted, needle exposed position and an extended needle protective or covered position.

The optional packaging cap 18 has a plurality of spaced prongs 20 adapted to form a friction fit with the interior surface of the outer distal end of the sleeve 14.

In the alternative, any releasable fitting, such as a threaded or snap fitting, is suitable for this use. When the needle guard 10 of FIGS. 1 and 2 is assembled for shipment by the manufacturer, bushing 16 mates with packaging cap 18. The cap 18 is removed when the syringe 12 is to be used.

The protective sleeve 14 is a hollow, molded plastic cylindrical tube. In the alternative, the sleeve 14 might have another shape, with an oval or polygonal cross section, for example, so long as its interior cross section is adequate to admit the barrel 22 of the syringe 12 and is cooperative with the bushing 16. Sleeve 14 includes guide means keyed to the bushing 16. In FIGS. 1 and 2, the guide means comprise straight longitudinal ribs 24a and 24b on the interior surface of sleeve 14, which coact with grooves 26a and 26b on the exterior surface of bushing 16 to prevent rotation of the sleeve 14 relative to bushing 16. Sleeve 14 also has means to limit axial movement of sleeve 14 relative to bushing 16, including two depressions or recesses 28a and 28b, located on the interior surface of sleeve 14 at its distal end near the packaging cap 18. Recesses 28a and 28b are adapted to engage radially outwardly extending members of fitting 16 such as lugs or tangs 30a and 30b. Tangs 30a and 30b are biased radially outwardly, and have the form of cantilever elastic members or beams. Tangs 30a and 30b terminate with radially outwardly extending lips or ridges 42a and 42b, respectively, that reversibly engage in recesses 28a and 28b or irreversibly engage with slots 34a and 34b in sleeve 14 as described below.

Sleeve 14 also has means for irreversibly locking the needle guard 10 in the extended position. As disclosed in FIGS. 1 and 2, such means comprise axial slots 34a and 34b located near the proximal end of sleeve 14, which are adapted to receive and irreversibly lock with the tangs 30a and 30b, and more particularly, the lips 42a and 42b. Sleeve 14 has a shoulder or an inwardly extending flange 32 at its proximal end for limiting movement of sleeve 14 on the busing 16 when the sleeve 14 is in the extended or needle guard position.

The fitting or bushing 16 has a generally annular shape with an exterior cylindrical surface 35 adapted to slidably cooperate with the interior surface of sleeve 14. Fitting 16 has an interior surface 36 adapted to form an interference or frictional fit with the lead portion 38 of the syringe barrel 22. An inwardly extending retaining flange 40 is provided to prevent lead portion 38 from being pushed through the bushing 16 entirely. In the alternative, the bushing 16 may be configured to form a threaded or snap fit with the lead portion 38 of the syringe barrel 22, or any other appropriate method of slidably coupling barrel 22 and fitting 16 may be used.

Bushing 16 preferably has two engageable members or tangs 30a, 30b, spaced about 180° from one another on the circumference and cooperative with respective detention depressions 28a, 28b on the inside of axially slidable sleeve 14. The lips 42a, 42b of tangs 30a and 30b thus reversibly engage depressions 28a, 28b of sleeve 14 when the sleeve 14 is in the retracted position to thereby hold sleeve 14 in place. When the sleeve 14 is slid in the direction of the needle 44 into the extended position, detent lips 42a, 42b irreversibly engage slots 34a, 34b spaced 180° apart and located near the proximal end of sleeve 14. Whether the lips 42a, 42b reversibly or irreversibly engage the sleeve 14 depends on the depth and shape of the engaging configuration or part of sleeve 14. Thus slots 34a, 34b have a depth and shape that insures that lips 42a, 42b are fully and irreversibly engaged.

Depressions 28a, 28b only partially engage lips 42a, 42b and this engagement can be overcome by a mild axial force.

The standard hypodermic syringe 12 of FIG. 2 has a detachable needle 44, and is, for illustration purposes, shown fully assembled in the ordinary fashion. Other commercially available hypodermic syringes have a unitary construction, so that the needle is fixed on the barrel. The embodiment of FIGS. 1 and 2 may be used with the fixed needle type of syringe. The user syringe barrel 22 into the proximal end of sleeve 14 through the opening formed by shoulder 32 is protective sleeve 14 until the lead portion 38 of the syringe barrel 22 engages the interior surface 36 and abuts the retaining flange 40 of bushing 16. The needle 44 protrudes through the bushing 16 into the packaging cap 18, which is hollow and may be provided with a passage 48 through its distal end to accommodate an overly long needle 44. Note, the cap 18 may then be reused.

After use, the user grasps the sleeve 14 and pushes it forward, breaking the engagement between lips 42a, 42b and depressions 28a, 28b. The user slides the sleeve 14 axially forward until detent members 42a, 42b engage slots 34a, 34b and shoulder 32 abuts bushing 16. The distal end of sleeve 14 now extends beyond the pointed tip of hypodermic needle 44, preventing any accidential injuries. The protected syringe may then be disposed of as a unit.

Figure 4:
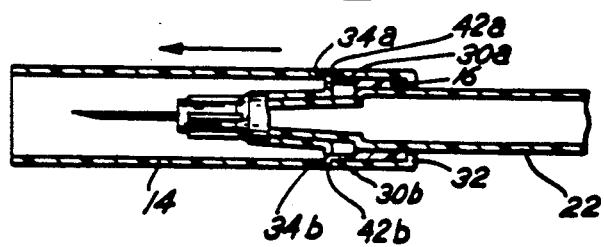
FIG. 4 is a partial sectional view of the second embodiment of the needle guard mounted on a hypodermic syringe with the sleeve in a locked extended position.

Turning now to FIGS. 3 and 4, a second embodiment of the present invention is depicted. In FIG. 3 the protective sleeve 14 is in the retracted position, and in FIG. 4 it is in the locked extended position. The interior surface 36 of bushing 16 is engaged with the lead portion 23 of the exterior surface of the syringe barrel 22. The distal end of the bushing 16 includes tangs 30a, 30b identical to the construction of the first embodiment. However, the second embodiment does not have the depressions 28a, 28b on the inside surface of the sleeve 14 as does the first embodiment so tangs 30a, 30b are not engaged. Thus as shown in FIG. 3, sleeve 14 is free to slide along bushing 16 and may be retracted to the point where it may lose contact with the bushing 16. However, as shown in FIG. 4, when sleeve 14 is moved to cover the needle, sleeve 14 is retained in position by tabs 42a, 42b, which are engaged with slots 34a, 34b of the sleeve 14 and also by shoulder 32 which abuts the proximate end of bushing 16.

FIGS. 5-7 disclose a third embodiment of the present invention, wherein like elements are given the same designations. The standard hypodermic syringe 12 in FIGS. 5-7 has a threaded connection between the barrel 22 and the needle 44, as opposed to the frictional fit exemplified in FIGS. 1-4. The barrel 22 thus includes a projecting connector or nipple 54 at one end which defines an annular space to receive a needle assembly by threaded attachment to an internally threaded tube 50. The hypodermic syringe barrel 22 therefore, has the outer tube portion 50 with internal threads 52 thereon. A bushing 17 has a unique construction which permits a frictional fit of counter base 58 with hollow connector member 54 rather than threaded engagement with threads 52. Sleeve 14 has grooves 60a, 60b with recesses 62a, 62b near the proximal end of sleeve 14. Bushing 17 has ribs 64a, 64b each terminating in tangs 66a, 66b, respectively, and each having tabs or lips 68a, 68b on the outside. Lips 68a, 68b ride in grooves 60a and 60b when the needle guard 10 is in the retracted position of FIG. 5. In the fully extended position of FIG. 6, lips 68a, 68b are forced into recesses 62a, 62b, locking sleeve 14 against further longitudinal movement. In the alternative, grooves 60a, 60b and recesses 62a, 62b may be replaced by a gradually diminishing slot such that ribs 64a, 64b are tightly wedged in the slots when the sleeve 14 is slid into the extended position. Bushing 17 is also provided with an outer annular forward nipple or annular counterbase 70 having internal threads 72. Flange 46 at the end of needle 44 threadedly engages threads 72.

After use, the needle 44 of this embodiment may be removed from the barrel 22 along with the needle guard 10 for disposal. The user merely grasps sleeve 14 and pulls, thereby breaking the frictional fit of hollow connector 54 with receiving portion 58 of bushing 17. If the hollow connector 54 is threaded to the barrel 22, the user merely twists sleeve 14 to break the threaded engagement. Thus, the barrel 22 and any contents of the barrel, such as blood samples drawn from a patient, are left intact.

Figure 8:
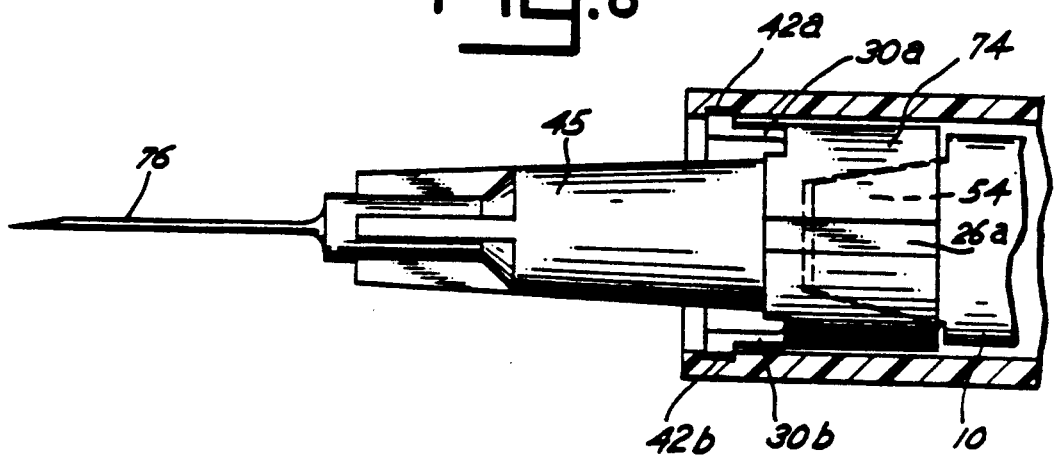
FIG. 8 is a sectional view of a fourth embodiment of the present invention, showing a hypodermic needle with a fitting or bushing formed as an integral part of the needle support.
Figure 9:
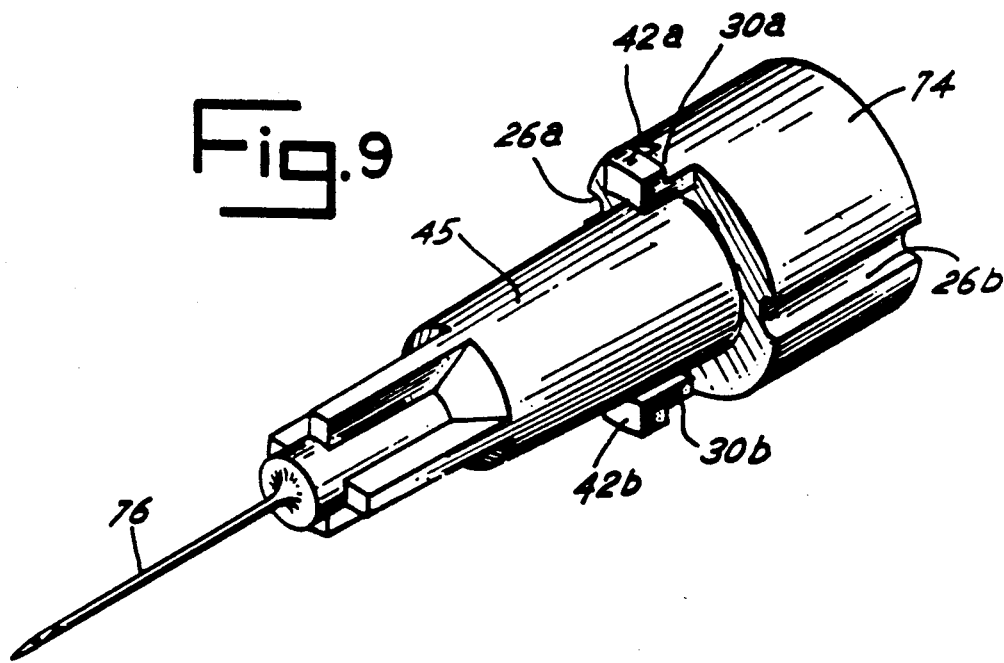
FIG. 9 is a perspective view of the fourth embodiment of the present invention, showing a hypodermic needle with the fitting formed as an integral part of the needle support.

Turning now to FIGS. 8 and 9, an alternative combination integral needle and bushing 45 is disclosed. It is formed with a base 74 having an outer configuration corresponding to that of bushing 16. The needle 76 is pre-packaged with the protective sleeve 14 in the retracted position by the manufacturer. The needle 76 is housed within the packaging cap 18 for storage and shipment. Thus, the needle base 74 has a generally annular shape with an exterior cylindrical surface adapted to fit within the interior surface of sleeve 14. Needle base 74 has grooves 26a, 26b which are capable of coacting with longitudinal ribs 24 on the interior surface of sleeve 14, and lugs or tangs 30a, 30b, which terminate with lips 42a, 42b and are capable of engaging both recesses 28a, 28b of sleeve 14 and also slots 34a, 34b of sleeve 14 as described above. In other words a bushing and needle construction are integrally molded as a single unit in the embodiment of FIGS. 8 and 9.

Although exemplary embodiments of the invention have been shown and described, many changes and substitutions may be made by one of ordinary skill in the art without departing from the scope of this invention. For example, although the sleeve is disclosed to be fully or partially translucent, it may be readily seen that the sleeve could be made of opaque materials except for a window or slot which allows the measure of the syringe to be read. In other applications, where it is not necessary to read a direct measurement off a syringe barrel, the shield may be completely opaque. This invention is suited for use with any medical or industrial instrument, such as intravenous needles or catheters, or other instruments which have a sharp point or blade. Other versions of this needle guard may be adapted for use with other types of syringes and medical implements without departing from the scope of this invention. This invention therefore includes alternatives to the specific configurations described in the exemplary embodiments and is limited only to the language of the claims.

What is claimed is:

1. A needle guard for a standard hypodermic syringe assembly of the type including a hypodermic needle and a barrel having a lead portion adjacent the hypodermic needle, the needle guard comprising an assembly which is attachable to the barrel and which in combination therewith maintains either a non-protective configuration or an irreversible protective configuration for the needle, said needle guard comprising in combination:

a needle base integrally formed with a needle, the needle base having an exterior portion and an interior portion, the interior portion being adapted to cooperatively mount in a fixed position on the lead portion of the barrel by frictionally, removably engaging the lead portion of the barrel;

a hollow protective sleeve on the needle base, said sleeve having an interior surface and exterior surface, the interior surface adapted to coact with the needle base;

guide means for slidably connecting the interior surface of said sleeve and the exterior portion of said needle base, said sleeve thereby being movable on the needle base axially in the direction of the length of the needle between a non-protective retracted position exposing the needle and a protective, extended position covering the needle; and means for irreversibly locking said sleeve only in the protective, extended position relative to said needle base, whereby axial and rotational movement of the sleeve relative to the needle base is prevented, and the sleeve in the protective, extended position protrudes beyond the tip of the needle such that the sleeve defines a guard which irreversibly prevents further access to the needle once the sleeve has been moved to the extended position;

wherein the means for irreversibly locking the sleeve in the extended position is comprised of at least one elastic axial rib located on the exterior surface of the needle base and terminating with an outwardly extending tang, the tang being biased radially outwardly by the rib to engage the sleeve, and the sleeve adapted to irreversibly engage the tang when the sleeve is axially positioned in the extended position.

2. The needle guard of claim 1 wherein the means for irreversibly locking the sleeve in the extended position is comprised of two elastic axial ribs located on the exterior surface of the needle base, spaced approximately 180 degrees apart, each terminating with an outwardly extending tang, the tang being biased radially outward by the rib to engage the sleeve, and the sleeve adapted to irreversibly engage the tangs when the sleeve is axially positioned in the extended position.

3. The needle guard of claim 1 wherein the guide means is comprised of two ribs distributed longitudinally along the interior surface of the sleeve and spaced approximately 180 degrees apart, and two slots located on the exterior portion of the fitting, spaced approximately 180 degrees apart and adapted to slidably coact with the ribs.

4. The needle guard of claim 1 wherein the means for irreversibly locking the sleeve in the extended position further comprises a depression on the interior surface of the sleeve near the distal end of the sleeve adapted to reversibly frictionally engage the tang, and a slot in the sleeve near the proximal end of the sleeve adapted to irreversibly frictionally engage the tang.

5. The needle guard of claim 1 wherein the rib extends axially from the fitting in the direction of the needle.

6. The needle guard of claim 1 wherein the rib extends axially from the fitting in the direction of the barrel.

7. A needle guard for a standard hypodermic syringe assembly of the type including a hypodermic needle and a barrel having a lead portion adjacent the hypodermic needle, the needle guard comprising an assembly which is attachable to the barrel and which in combination therewith maintains either a non-protective or a protective configuration for the needle, said needle guard comprising in combination:

a needle base having an exterior portion and an interior portion, the interior portion being adapted to cooperatively mount in a fixed position on the lead portion of the barrel by frictionally, removably engaging the lead portion of the barrel;

a hollow, protective sleeve on the needle base, said sleeve having an interior surface and an exterior surface, the interior surface adapted to coact with the needle base;

guide means for slidably connecting the interior surface of said sleeve and the exterior portion of said needle base, said sleeve thereby being movable on the needle base axially in the direction of the length of the needle between a non-protective retracted position exposing the needle and a protective, extended position covering the needle; and means for retaining said sleeve in the protective, extended position covering the needle, said means for retaining being comprised of at least one elastic, cantilevered rib located on the exterior surface of the needle base extending axially from the needle base in the direction of the needle and biased for locking engagement with the sleeve, and an outwardly extending tang, the tang being biased radially outward by the rib to engage the sleeve, and the sleeve being adapted to engage the tang in the extended position.

8. The needle guard of claim 7 wherein the retaining means comprises means for irreversible locking engagement of the sleeve and needle base in the extended position.

9. A needle guard for a standard yhypodermic syringe assembly of the type including a hypodermic needle and a barrel having a lead portion adjacent the hypodermic needle, the needle guard comprising an assembly which is attachable to the barrel and which in combination therewith maintains either a non-protective or a protective configuration for the needle, said needle guard comprising in combination;

a needle base integrally formed with a needle, the needle base having an exterior portion and an interior portion, the interior portion being adapted to cooperatively mount in a fixed position on the lead portion of the barrel by frictionally, removably engaging the lead portion of the barrel;

a hollow protective sleeve on the needle base, said sleeve having an interior surface and exterior surface, the interior surface adapted to coact with the needle base;

guide means for slidably connecting the interior surface of said sleeve and the exterior portion of said needle base, said sleeve thereby being movable on the needle base axially in the direction of the length of the needle between a non-protective retracted position exposing the needle and a protective, extended position covering the needle;

means for irreversibly locking said sleeve only in the protective, extended position relative to said needle base; and means for removing the needle and needle guard from the barrel, leaving the barrel and any contents of the barrel intact, whereby axial and rotational movement of the sleeve relative to the needle base is prevented, and the sleeve in the protective, extended position protrudes beyond the tip of the needle such that the sleeve defines a guard which irreversibly prevents further access to the needle once the sleeve has been moved to the extended position;

wherein the means for removing the needle and needle guard from the barrel is comprised of at least one elastic axial rib located on the exterior surface of the needle base and terminating with an outwardly extending tang, the tang being biased radially outward by the rib to engage the sleeve, the sleeve being adapted to irreversibly engage the tang when the sleeve is axially positioned in the extended position; a depression on the interior surface of the sleeve near the distal end of the sleeve adapted to reversibly frictionally engage the tang; and a slot in the sleeve near the proximal end of the sleeve adapted to irreversibly frictionally engage the tang.

* * * * *